United States Patent
Fried et al.

(10) Patent No.: US 7,137,395 B2
(45) Date of Patent: Nov. 21, 2006

(54) CIRCUMFERENTIAL PULMONARY VEIN ABLATION USING A LASER AND FIBEROPTIC BALLOON CATHETER

(75) Inventors: Nathaniel M. Fried, Baltimore, MD (US); Henry R. Halperin, Baltimore, MD (US); Ronald D. Berger, Pikesville, MD (US); Albert C. Lardo, Baldwin, MD (US); Arkadiy Tsitlik, Reisterstown, MD (US)

(73) Assignee: The Johns Hopkins University, Baltimore, MD (US)

( * ) Notice: Subject to any disclaimer, the term of this patent is extended or adjusted under 35 U.S.C. 154(b) by 255 days.

(21) Appl. No.: 09/796,571

(22) Filed: Feb. 28, 2001

(65) Prior Publication Data
US 2002/0052621 A1 May 2, 2002

Related U.S. Application Data
(60) Provisional application No. 60/185,622, filed on Feb. 29, 2000.

(51) Int. Cl.
*A61B 19/00* (2006.01)
(52) U.S. Cl. ............... 128/898; 606/191; 607/122
(58) Field of Classification Search ............ 606/2, 606/13–17, 27–34, 191–194; 607/100–105, 607/115, 116, 119, 122, 123; 128/898
See application file for complete search history.

(56) References Cited

U.S. PATENT DOCUMENTS

| | | | |
|---|---|---|---|
| 4,799,479 A | 1/1989 | Spears | 128/303 |
| 5,114,423 A * | 5/1992 | Kasprzyk et al. | 606/27 |
| 5,140,987 A | 8/1992 | Schuger et al. | 128/642 |
| 5,344,419 A | 9/1994 | Spears | 606/15 |
| 5,500,012 A * | 3/1996 | Brucker et al. | 607/122 |
| 5,540,679 A | 7/1996 | Fram et al. | 606/27 |
| 5,553,611 A * | 9/1996 | Budd et al. | 600/374 |
| 5,833,682 A | 11/1998 | Amplatz et al. | 606/15 |
| 6,012,457 A * | 1/2000 | Lesh | 128/898 |
| 6,325,797 B1 * | 12/2001 | Stewart et al. | 606/41 |
| 6,572,609 B1 * | 6/2003 | Farr et al. | 606/15 |
| 2002/0183738 A1 * | 12/2002 | Chee et al. | 606/41 |

FOREIGN PATENT DOCUMENTS

WO  WO 01/03599  1/2001

OTHER PUBLICATIONS

PCT Search Report.

* cited by examiner

Primary Examiner—Henry Bennett
Assistant Examiner—Dinnatia Doster-Greene
(74) Attorney, Agent, or Firm—Edwards Angell Palmer & Dodge LLP; Peter F. Corless; Lisa Swiszcz Hazzard

(57) ABSTRACT

A balloon catheter device that provides radial delivery of visible or near-infrared radiation. The radial delivery of visible or near-infrared radiation to the pulmonary vein is particularly effective in creating transmural, continuous, and circumferential lesions in the pulmonary vein. Creation of these lesions electrically isolates the pulmonary veins from the left atrium of the heart and, thus is a particularly suitable method for the treatment of atrial fibrillation.

47 Claims, 4 Drawing Sheets

Focal Ablation

Spot Welding

Circumferential Ablation

Figure 3. Circumferential pulmonary vein (PV) ablation using a laser and fiberoptic balloon catheter.
(a) Surface photo of the four PV at the LA-PV interface.
(b) Trichrome-stained photomicrograph cross-section of PV#2, a control, appears pink.
(c,d) Cross-section and length of ablated PV#4 appears blue.

CIRCUMFERENTIAL PULMONARY VEIN ABLATION USING A LASER AND FIBEROPTIC BALLOON CATHETER

The present application claims the benefit of U.S. provisional application No. 60/185,622, filed on Feb. 29, 2000, incorporated herein by reference.

FIELD OF THE INVENTION

The present invention generally relates to surgical methods and devices for the delivery of laser radiation and, more particularly, to methods and devices for radial delivery of radiation, preferably visible or near-infrared radiation. The devices and methods are particularly suitable for the treatment of arrhythmias, and, in particular, catheter ablation of aroxysmal atrial fibrillation.

BACKGROUND OF THE INVENTION

The sinus node is known as the heart's "natural pacemaker". The sinus node sends out electrical signals to the lower chambers of the heart (ventricals), causing the chambers to contract at a steady rhythm of about 60 to 100 beats per minute.

When the heart is not beating at a steady rate, the irregular heartbeats are called arrhythmias. The most common type of sustained arrhythmia is atrial fibrillation. Atrial fibrillation (AF) is a rapid, irregular heart rhythm caused by abnormal electrical signals from the upper chambers of the heart (atrium). AF may increase the heart rate to and in excess of 100 to 175 beats per minute. As a result, the atria quiver rather than contracting normally, which can result in blood pooling in the atria, the formation of blood clots and strokes.

Recent studies suggest that the pulmonary veins (PV) are a major source of paroxysmal atrial fibrillation (AF) (Haissaguerre M, Jais P. Shah DC, Takahashi A, Hocini M, Quiniou G. Garrigue S. Le Mouroux A, Le Metayer P. Clementy J. Spontaneous initiation of atrial fibrillation by ectopic beats originating in the pulmonary veins. *N Eng J Med* 1998;339:659–66).

One method for treating AF is to burn out, freeze or surgically excise the tissues and pathways from which the abnormal signals arise (ablation).

Radiofrequency (RF) catheter ablation of arrythmogenic sites inside the pulmonary veins (FIG. 1a) has proven successful in eliminating recurrence of AF. However, difficulty in locating arrythmogenic foci and complications during RF ablation such as thrombus formation and pulmonary vein stenosis have limited the efficacy of this procedure. (Robbins IM, Colvin EV, Doyle TP, Kemp WE, Loyd JE, McMahon WS, Kay GN. Pulmonary vein stenosis after catheter ablation of atrial fibrillation. *Circulation* 1998;98: 1769–1775; Chen SA, Hsieh MH, Tai CT, Tsai CF, Prakash VS, Yu WC, Hsu TL, Ding YA, Chang MS. Initiation of atrial fibrillation by ectopic beats originating from the pulmonary veins: electrophysiological characteristics, pharmacological responses, and effects of radiotrequency ablation. *Circulation* 1999;100: 1879–86; Shah DC, Haissaguerre M, Jais P. Catheter ablation of pulmonary vein foci for atrial fibrillation: PV foci ablation for atrial fibrillation. *Thorac Cardiovasc Surg* 1999;47 (Suppl 3):352–6; Hsieh MH, Chen SA, Tai CT, Tsai CF, Prakash VS, Yu WC, Liu CC, Ding YA, Chang MS. Double multielectrode mapping catheters facilitate radioirequency catheter ablation of focal atrial fibrillation originating from pulmonary veins. *J Cardiovasc Electrophysiol* 1999; 10:136–44).

For example, Shah et al. reported a 69% success rate in 110 patients, with 4% of the pulmonary veins showing stenosis after 8±4 months. (Shah DC, Haissaguerre M, Jais P. Catheter ablation of pulmonary vein foci for atrial fibrillation: PV foci ablation for atrial fibrillation. *Thorac Cardiovasc Surg* 1999;47 (Suppl 3):352–6). Chen et al. reported similar success rates of 86% in 68 patients, but with a much higher frequency (42%) of pulmonary vein stenosis after 6±2 months. (Chen SA, Hsieh MH, Tai CT, Tsai CF, Prakash VS, Yu WC, Hsu TL, Ding YA, Chang MS. Initiation of atrial fibrillation by ectopic beats originating from the pulmonary veins:electrophysiological characteristics, pharmacological responses, and effects of radiotrequency ablation. *Circulation* 1999;100: 1879–86). In a case study involving 18 patients, Robbins, et al. found pulmonary stenosis with severe pulmonary hypertension in 2 patients (11%) after 3 months, and concluded that the use of standard catheter technology for RF ablation of the pulmonary veins should be avoided. (Robbins IM, Colvin EV, Doyle TP, Kemp WE, Loyd JE, McMahon WS, Kay GN. Pulmonary vein stenosis after catheter ablation of atrial fibrillation. *Circulation* 1998; 98: 1769–1775).

Another limitation of RF focal ablation is its inability to produce conduction block in a single application. Frequently, it is difficult to locate and effectively ablate the arrythmogenic foci. For example, Haissaguerre et al. reported the need for 5±5 RF ablation applications of from 60–120 seconds for each focus (Haissaguerre M, Jais P. Shah DC, Takahashi A, Hocini M, Quiniou G. Garrigue S. Le Mouroux A, Le Metayer P. Clementy J. Spontaneous initiation of atrial fibrillation by ectopic beats originating in the pulmonary veins. *N Eng J Med* 1998;339:659–66), while Chen et al. reported the need for 7±3 RF ablation applications of from 20–40 seconds. (Chen SA, Hsieh MH, Tai CT, Tsai CF, Prakash VS, Yu WC, Hsu TL, Ding YA, Chang MS. Initiation of atrial fibrillation by ectopic beats originating from the pulmonary veins: electrophysiological characteristics, pharmacological responses, and effects of radiotrequency ablation.*Circulation* 1999;100: 1879–86).

The limitations of RF focal ablation (FIG. 1a) have elicited the exploration of alternative ablation strategies.

One alternative approach is to electrically isolate the pulmonary veins from the left atrium by creating a circumferential line of conduction block at the PV ostia. RF energy has been used to create a contiguous line of conduction block from a series of discrete circular RF lesions, or 'spot welds' (FIG. 1b) (Schwartzman D. Circumferential radiobrequency ablation of pulmonary vein orifices: feasibility of a new technique. *PACE* 1999;22:711). However, spot welding may be tedious and ineffective because the creation of a contiguous circumferential lesion from a series of precisely placed individual RF lesions is difficult to achieve under the current imaging limitations of x-ray fluoroscopy. Furthermore, even in cases when good electrode-tissue contact can be achieved, RF heating produces superficial direct heating due to a rapid attenuation of the electrical current density with tissue depth, resulting in a steep temperature gradient in the subsurface tissue layers. The combination of poor electrode-tissue contact due to imaging limitations and steep temperature gradients may increase the probability of complications such as tissue vaporization, endothelial disruption, and coagulum formation. Endothelial disruption may be responsible for incidents of pulmonary vein stenosis which have been reported during previous pulmonary vain ablation studies using RF energy. (Robbins IM, Colvin EV, Doyle TP, Kemp WE, Loyd JE, McMahon WS, Kay GN. Pulmonary vein stenosis after catheter ablation of atrial fibrillation. *Circulation* 1998;98:1769–1775; Chen SA, Hsieh MH, Tai CT, Tsai CF, Prakash VS, Yu WC, Hsu TL, Ding YA, Chang MS. Initiation of atrial fibrillation by ectopic beats originating from the pulmonary veins: electrophysiological characteristics, pharmacological responses, and effects of radiotrequency ablation. *Circulation* 1999; 100: 1879–86; Shah DC, Haissaguerre M, Jais P. Catheter ablation. of pulmonary vein foci for atrial fibrillation: PV foci ablation for atrial fibrillation. *Thorac Cardiovasc Surg* 1999;47 (Suppl 3):352–6; Hsieh MH, Chen SA, Tai CT, Tsai CF, Prakash VS, Yu WC, Liu CC, Ding YA, Chang MS. Double multielectrode mapping catheters facilitate radioirequency catheter ablation of focal atrial fibrillation originating from pulmonary veins. *J Cardiovasc Electrophysiol* 1999; 10: 136–44).

SUMMARY OF THE INVENTION

The present invention provides a device and method for the treatment of arrhythmias, and, in particular, aroxysmal atrial fibrillation. More particularly, the present invention provides a balloon catheter device that radially delivers visible or near-infrared radiation to the pulmonary veins. This radial delivery matches the cylindrical anatomy of the pulmonary veins (FIG. 1c). The balloon catheter device may be used to electrically isolate the pulmonary veins from the left atrium of the heart by creating transmural, continuous, and circumferential lesions at the PV ostia in a single application. Further, use of near-infrared laser radiation enables deeper penetration into cardiac tissue as compared to RF energy, provides more uniform tissue heating and less probability of complications such as tissue vaporization, endothelial disruption, and coagulum formation.

An exemplary embodiment of the device includes a sheath that houses an optical fiber. At the tip of the sheath is a balloon that is inflated when the device reaches its target site. Inflation of the balloon distends the pulmonary vein walls and locks the balloon catheter device into place, displaces blood allowing efficient coupling of radiation into the tissue and prevents coagulum formation during irradiation.

A method for the treatment of arrhythmias, particularly aroxysmal atrial fibrillation, is also disclosed. The method comprises providing a balloon catheter device that radially delivers visible or near-infrared radiation, inserting the balloon catheter device to the target site (pulmonary vein), inflating the balloon, and applying the visible or near-infrared radiation to electrically isolate the pulmonary veins from the left atrium of the heart. Electrical isolation may be accomplished by forming continuous or partial lesions in the pulmonary veins.

Other aspects and embodiments of the invention are discussed infra.

DETAILED DESCRIPTION OF THE INVENTION

Figure 1A:
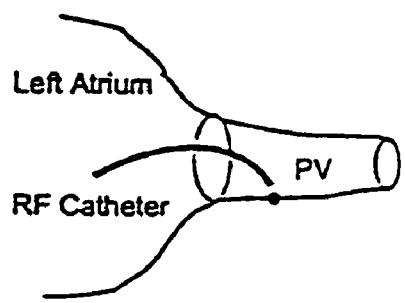
FIG. 1a shows a prior method of focal ablation of an arrythmogenic foci inside the pulmonary vein using an RF catheter.
Figure 1B:
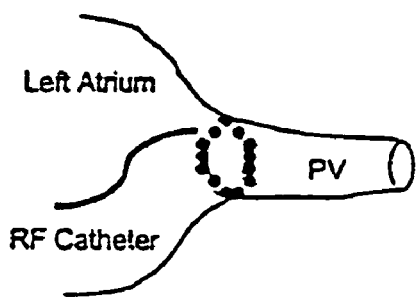
FIG. 1b shows a prior art method of electrical isolation of the pulmonary vein from the left atrium by creating a continuous circumferential lesion at the PV ostia from a series of discrete circular RF lesions.
Figure 1C:
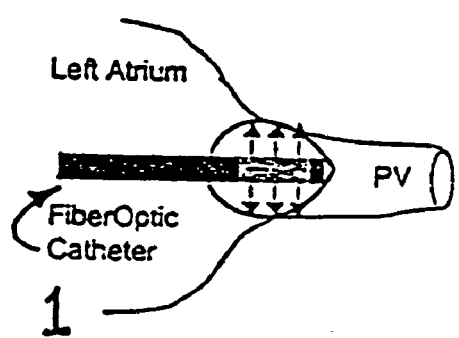
FIG. 1c shows the creation of a continuous circumferential line of conduction block in a single application by radial delivery of laser energy through a fiberoptic balloon catheter, in accordance with the present invention.

Referring now to the various figures of the drawing, wherein like reference characters refer to like parts, there is shown various views of a balloon catheter device 1, in accordance with the invention.

The balloon catheter device 1 includes generally a sheath 2 having a proximal end 4 and a distal end 6, a balloon 8 mounted on the distal end 6 of the sheath 2, an optical fiber 10 extending through the sheath 2 and into the balloon 8 and a high-power source, such as a laser (not shown), of visible or near-infrared radiation.

The dimensions of the balloon catheter device 1 may vary depending on its ultimate use. For example, in a preferred embodiment, the sheath 2 is designed for insertion into the pulmonary veins for the treatment of aroxysmal atrial fibrillation. This is typically accomplished by numbing an area the patient's upper thigh and inserting the balloon catheter device 1 through a blood vessel (usually in the upper thigh) and all the way up to the heart. As such, the sheath 2 is designed to provide access from the area of insertion to the heart, and preferably has a length ranging from about 20 cm to about 80 cm, more preferably, from about 50 cm to about 60 cm. Of course, the length of the sheath 2 may vary depending on the point of insertion and the distance from the point of insertion to the target site. Further, to enable insertion of the sheath 2 through the blood vessel to the pulmonary vein of the heart, the sheath 2 must be appropriately sized. As such, the sheath 2 preferably has outer diameter that ranges from about 2 mm to about 4 mm (preferably less than 10 Fr). The inner diameter of the sheath 2 may vary depending on the size of the optical fiber 10 that is used and preferably ranges from about 3 to about 6 Fr (about 1 to about 2 mm).

In a preferred embodiment, the balloon catheter device 1 may further include a water-tight valve 12 at the proximal end 4 of the sheath 2 for introducing the optical fiber 10 into the sheath 2 and locking the optical fiber 10 into place once the distal tip 11 of the optical fiber 10 is aligned and centered inside the balloon 8. The balloon catheter device 1 may further include a second valve 14 that enables balloon inflation from an external source. For example, a syringe or similar mechanism may be connected to the second valve 14 such that water, saline, contrast agent or similar material may be injected through the sheath 2 and into the balloon 8.

To assist injection of the water, saline, contrast agent or similar material into the balloon 8, an inflation lumen 16 between the sheath 2 and optical fiber 10 may form a channel through which the water, saline, contrast agent or similar material may travel. In a preferred embodiment, the inflation lumen 16 has a diameter ranging from about 100 to about 500 μm for proper balloon inflation.

In applications where the balloon catheter device 1 is inserted and guided through a blood vessel towards a target site, guidewires 18 may further be incorporated into the sheath 2 for steerable guidance of the balloon catheter device 1 into the pulmonary veins.

Balloons used in balloon catheter devices are well known and, thus, although described and shown with reference to a preferred embodiment, the general features (e.g. size, shape, materials) of the balloon 8 may be in accordance with conventional balloons. In a preferred embodiment, the balloon 8 is made of an optically transparent, flexible medical-grade silicone rubber and is capable of being inflated to a 5-cc-volume, 2-cm-diameter and 4-cm-length. Alternatively, the balloon 8 may be made of other materials, such as polyethylene terepthalate (PET), as long as it is optically transparent to the laser radiation, biocompatible, and distendable.

The balloon 8 is preferably attached directly to the distal end 6 of the sheath 2 and is preferably compressed to the diameter of the sheath 2 for insertion of the balloon catheter device 1 into the body. The balloon 8 serves to distend the pulmonary vein walls locking the balloon catheter device 1 in place. The balloon 8 further displaces blood allowing efficient coupling of radiation into the tissue and preventing coagulum formation during irradiation. Additionally, the balloon 8 is preferably inflated by filling the balloon 8 with water, saline, contrast agent, or other optically transparent solutions to provide cooling of the optical fiber 10 during irradiator, and to allow tracking under x-ray, ultrasound, or MRI guidance.

A high-power source of visible or near-infrared radiation (preferably $\lambda=400–1300$ nm), such as a laser, is further included in the present invention. When the device is used on the pulmonary veins for the treatment of aroxysmal atrial fibrillation, a high power laser that provides approximately 10–100 W is preferably used to effectively produce thermal lesions in the pulmonary veins. The laser wavelength may be chosen to minimize radiation absorption by water or other material inside the balloon and in the tissue, and maximize radiation penetration into the pulmonary vein walls for uniform heating. For example, a high-power diode laser array operating between about 600–1300 μm, Nd:YAG lasers operating at about 1.06 or 1.32 μm, or fiber lasers operating near 1 μm would be appropriate laser sources for heating the pulmonary veins. The laser could be operated in either continuous-wave mode, long-pulse mode (1–10 seconds), or short-pulse mode (<1 μs) with high pulse repetition rate (100–1000 Hz) achieving quasi-CW operation.

Optical fibers are well known and, thus, although described and shown with reference to a preferred embodiment, the general features (e.g. size, shape, materials) of the optical fiber 10 may be in accordance with conventional optical fibers. For example, optical fibers are commercially available in a number of core sizes (100–600 μm), outer diameters (0.4–1.9 mm), and diffusing tip lengths (5–100 mm). The present device may utilize optical fibers 10 with larger diameters, which provide higher power transmission. However, larger diameter fibers provide decreased flexibility. Thus, in some cases, a smaller diameter optical fiber 10 having increased flexibility may be desired to provide ease in accessing a difficult to reach target site. In other cases, a larger diameter optical fiber 10 may be used if, for example, a more direct access to the site is utilized. Further, transmission through the fibers is dependent on fiber length, but ranges between 80–90% of input laser power, with 3–7% variations in transmission along the diffusing tip. In a particularly preferred embodiment, for pulmonary vein ablation, the optical fiber 10 is made of a silica core and cladding protected with a teflon-coated jacket. Preferably, the optical fiber 10 has a has a core size that ranges from about 400 to about 600 μm, and a tip length ranging from about 5 to about 20 mm.

The balloon catheter device 1 is designed for radial delivery of the radiation, which matches the cylindrical anatomy of the pulmonary veins. Thus, the balloon catheter device 1 further includes a radial delivery mechanism.

In one embodiment, the radial delivery mechanism comprises scattering particles embedded in the optical fiber 10. For example, the optical fiber 10 may be made of a flexible silicone elastomer with a gradient of titanium dioxide scattering particles embedded in the active distal tip 11 of the optical fiber 10. Alternatively, other types of scattering particles, such as those made of aluminum oxide, may also be used. These scattering particles provide near uniform 360 degree delivery of the radiation over the tip length.

In another embodiment, the radial delivery mechanism comprises a frosted cap (not shown) placed over the distal tip 11 of the optical fiber 10. For example, the core of the optical fiber 10 may first be exposed by an acid etching technique, followed by placement of a frosted cap over the active distal tip 111 of the optical fiber 10. Such frosted caps are well are well known and may be in accordance with conventional frosted caps. The frosted cap serves both to scatter the radiation into a uniform beam profile and to protect the exposed silica core from damage. Although the beam profile along the active fiber tip length is not as uniform (20–40% variation) as an optical fiber design utilizing embedded scattering particles, scattering produced by both the frosted cap and the tissue itself serves to smoothen inhomogeneities in the beam profile.

Figure 2:
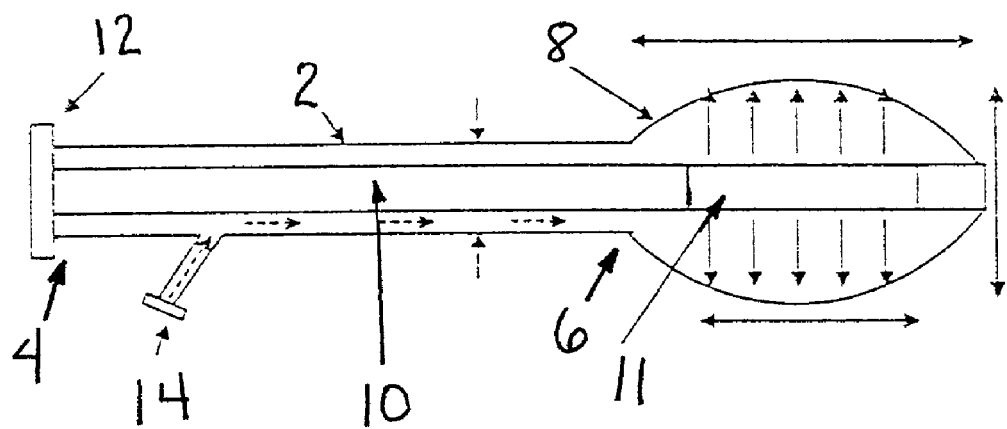
FIG. 2 shows an embodiment of the surgical device in accordance with the present invention.
Figure 4:
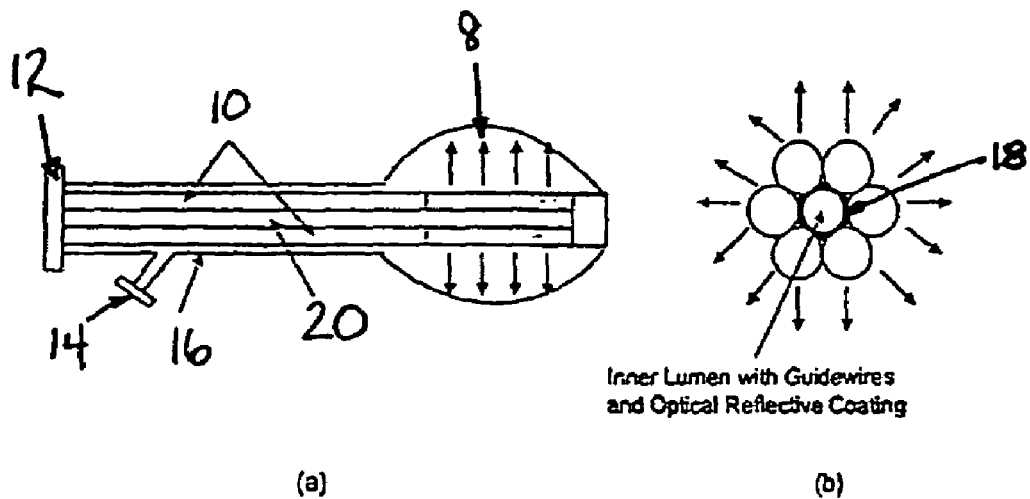
FIG. 4 shows another embodiment of the surgical device in accordance with the present invention, wherein a ring of diffusing fibers is located around a central lumen.

In another embodiment, the radial delivery mechanism comprises a cluster of diffusing optical fibers. For example, rather than use a single diffusing optical fiber 10 (FIG. 2), a ring of smaller optical fibers 10 is used (FIG. 4). In a preferred embodiment, a guidewire 18 housed within a guidewire lumen 20 is surrounded by a ring of diffusing optical fibers 10.

Figure 5:
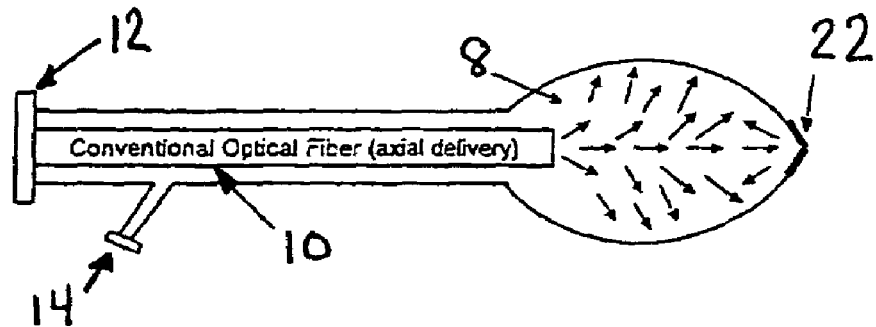
FIG. 5 shows another embodiment of the surgical device in accordance with the present invention, wherein radiation is delivered axially and then scattered uniformly by scattering solution in the balloon.

In yet another embodiment, the radial delivery mechanism comprises an optically scattering solution. For example, the optically scattering solution may be injected into the balloon 8 to inflate the balloon. The optically scattering solution within the balloon 8 then uniformly scatters radiation delivered axially from a conventional optical fiber (FIG. 5). As shown in FIG. 5, a reflective tip 22 may further be located at the distal side of the balloon 8 to assist in diverting radiation delivered axially from the optical filer 10.

Figure 6:
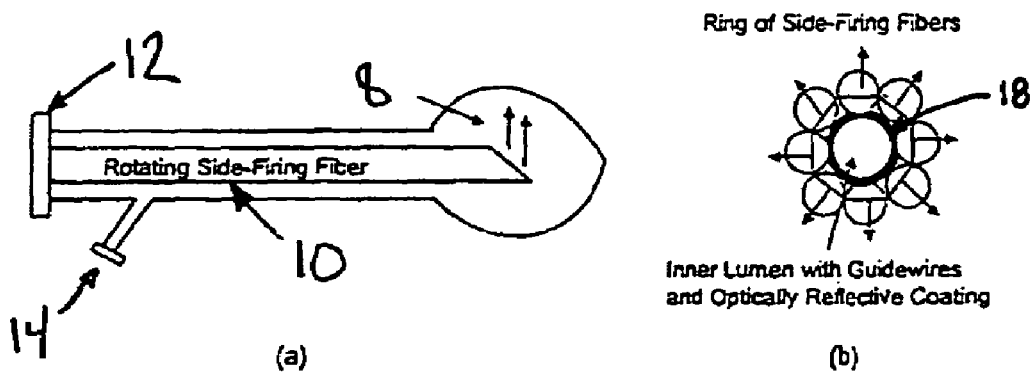
FIG. 6 shows another embodiment of the surgical device in accordance with the present invention, having either a single rotating side-firing optical fiber or a ring of side-firing fibers.

In another embodiment, the radial delivery mechanism comprises side-firing optical fibers, as shown in FIG. 6, that deliver radiation at a 90 degree angle from the axis of the optical fiber 10. For example, a single side-firing optical fiber 10 could be used and rotated (FIG. 6a) to produce a continuous lesion. Alternatively, ring of fixed side-firing optical fibers 10 could be used (FIG. 6b) to produce a continuous lesion. In a preferred embodiment, the ring of side-firing optical fibers 10 surrounds a guidewire 18 housed within a guidewire lumen 20.

Alternatively, a combination of the radial delivery mechanism designs shown in FIGS. 2, 4, 5, and 6 may be used to radially deliver radiation to electrically isolate the pulmonary veins from the left atrium of the heart.

In accordance with the present method for treating aroxysmal atrial fibrillation, the pulmonary veins are electrically isolated from the left atrium, thereby preventing the abnormal electrical signals from reaching lower chambers of the heart. Preferably, to determine whether the pulmonary veins have been electrically isolated from the left atrium, electrical measurements are made. These measurements may be made at any time before, during and after the procedure to determine when electrical isolation is accomplished. In a preferred embodiment, electrodes are painted onto the surface of the balloon 8 to provide good electrode-tissue contact once the balloon distends the pulmonary vein walls.

Further, it is important during the procedure to regulate the ablation parameters, ensuring that transmural lesions are achieved without overheating the tissue, which could result in coagulum formation, tissue vaporization, and pulmonary vein stenosis. Preferably, the ablation proceeds at a temperature in the range of about 50–80° C. Thus, a temperature measurement mechanism is preferably included in the device to provide active feedback to the laser system. In a preferred embodiment, the temperature measurement mechanism is in the form of thermocouples, which may be embedded in the balloon wall.

The balloon catheter device 1 is generally used by the following procedure: the balloon catheter device 1 is assembled (or it may come preassembled) with the optical fiber 10 extending through the sheath 2 and into the balloon 8. The water-tight valve 12 is adjusted to lock the optical fiber 10 into place. The balloon 8 is preferably compressed to the sheath diameter 2 for easier insertion of the balloon catheter device 1 into the body. An incision is made to provide access to the target site. For example, an incision may be made in the patient's upper thigh and the balloon catheter device 1 inserted through a blood vessel in the upper thigh and directed all the way up to the heart. To assist in guiding balloon catheter device 1 through the blood vessel to the pulmonary vein, a guidewire 8 within the device may be used. When the balloon catheter device 1 reaches the target site, a syringe or similar balloon inflation source is connected to the device, for example, by connecting the syringe to valve 14 and pushing the syringe plunger to inject water, saline, contrast agent or similar material into the balloon 8. Once the balloon 8 has been inflated, electrical measurements may be made at any point during the procedure. The high-power source of visible or near-infrared radiation, such as a laser, is then activated and radiation emitted radially from the optical fiber 10. If a single side-firing optical fiber is used, as described above, the optical fiber is then rotated to radially deliver the radiation. Prior to removal of the balloon catheter device 1, an electrical measurement is made to ensure that electrical isolation has been accomplished.

The present invention also includes kits that comprise one or more device of the invention, preferably packaged in sterile condition. Kits of the invention also may include syringes, saline, contrast agents, guidewires, etc. for use with the device, preferably packaged in sterile condition, and/or written instructions for use of the device and other components of the kit.

All documents mentioned herein are incorporated by reference herein in their entirety. The following non-limiting examples are illustrative of the invention.

EXAMPLES

Figure 3:
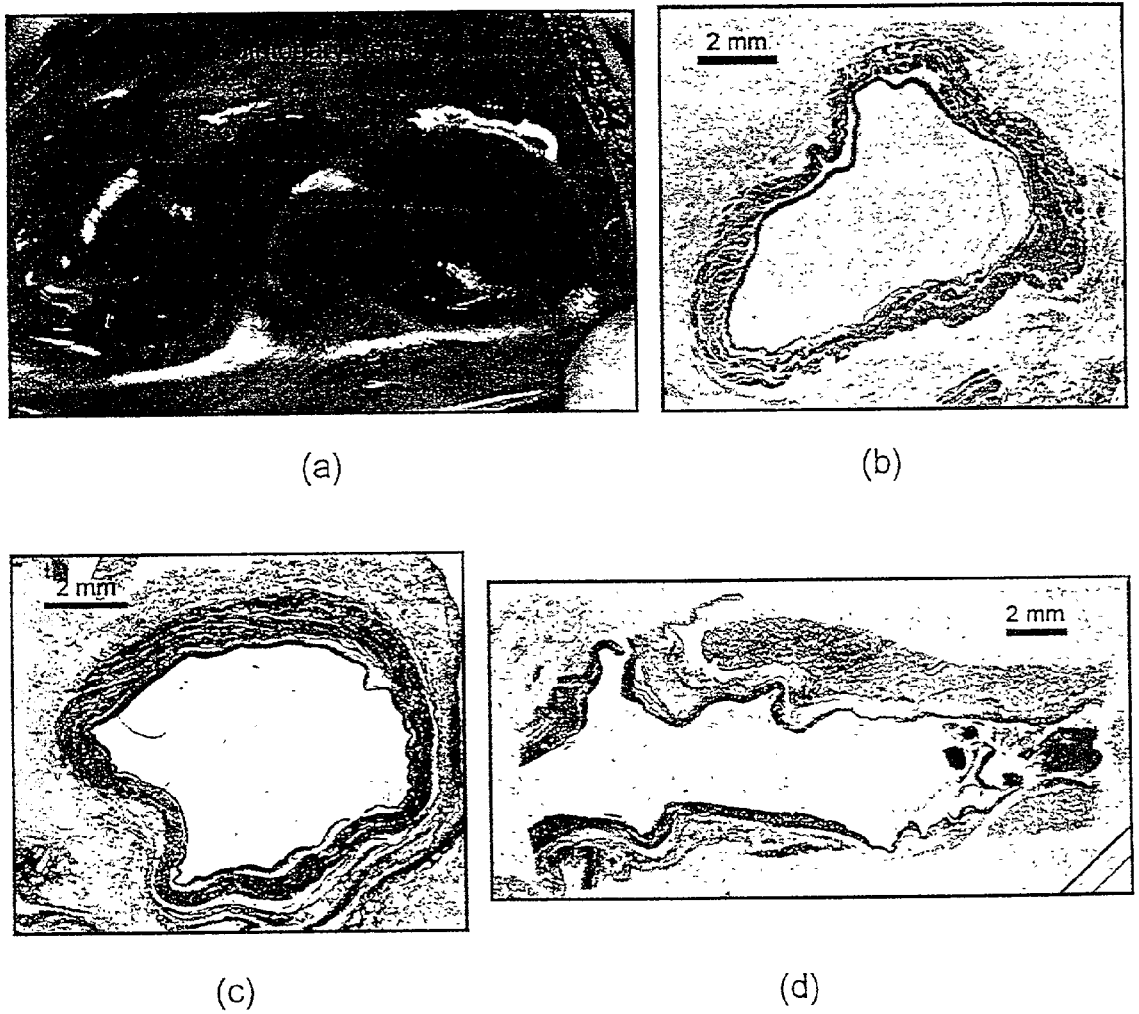
FIGS. 3a–3d shows circumferential pulmonary vein (PV) ablation using a laser and fiberoptic balloon catheter in accordance with the present invention wherein: 3a shows a surface photo of the four PV at the LA-PV interface; 3b shows a trichrome-stained photomicrograph cross-section of PV#2, a control, appears pink; and 3c–3d show a cross-section and length of ablated PV#4 appears blue.

Preliminary pulmonary vein ablation experiments were performed in dogs, in vivo. During an open-chest procedure, the left atrial appendage was punctured, and the balloon catheter was placed into the left atrium. The balloon was filled with an optically transparent, radiopaque solution and the catheter was placed into the pulmonary veins under x-ray fluoroscopic guidance. Continuous-wave, 1.06-µm, Nd:YAG laser radiation was coupled into a 600-µm-core, 1.5 mm-OD optical fiber with a 2-cm-long radial diffusing tip. The fiber tip was placed inside a silicone rubber balloon, inflated to a 15-mm-diameter and a 30-mm-length under tension in the pulmonary veins. Continuous, circumferential lesions were created at the left atria-pulmonary vein interface using a laser power of 50 W and an irradiation time of 90 s. Three out of four pulmonary veins were ablated with a nonsteerable catheter demonstrating the ease of accessing the pulmonary veins from the left atrium (FIG. 3).

The foregoing description of the invention is merely illustrative thereof, and it is understood that variations and modifications can be effected without departing from the scope or spirit of the invention as set forth in the following claims.

What is claimed is:

1. A balloon catheter device suitable for treating arrhythmias attributable to atrial fibrillation; said balloon catheter device comprising:

a shaft having a proximal end and a distal end;

a balloon at the distal end of the shaft;

wherein the balloon is configured and arranged so as to be in a deflated state when the balloon is being maneuvered and positioned proximal a pulmonary vein proximal the left atrium and is configured and arranged so when the balloon is in an inflated state the balloon is removably secured within the pulmonary vein proximal the left atrium;

at least one optical fiber that extends through the shaft and the balloon; and a radial delivery mechanism positioned inside of the balloon, wherein the radial delivery mechanism and at least one optical fiber are arranged so that visible or near-infrared radiation is radially delivered from the optical fiber to a portion of the pulmonary vein proximal the optical fiber, and at a power level sufficient to cause at least one of transmural, continuous and circumferential lesions to be formed in the pulmonary vein and thereby electrically isolating the pulmonary vein from the left atrium.

2. The balloon catheter device of claim 1, wherein the treatment, electrical isolation or lesions are achieved in a single application.

3. The balloon catheter device of claim 1, wherein the balloon catheter device includes a sheath that has a length greater than about 20 cm.

4. The balloon catheter device of claim 3, wherein the sheath has a length ranging from about 50 cm to about 60 cm.

5. The balloon catheter device of claim 3, wherein the sheath has an outer diameter that ranges from about 2 mm to about 4 mm.

6. The balloon catheter device of claim 5, wherein the sheath has an outer diameter less than about 10 Fr.

7. The balloon catheter device of claim 3, wherein the sheath has an inner diameter ranging from about 3 to about 6 Fr.

8. The balloon catheter device of claim 3, further including a valve at the proximal end of the sheath for introducing an optical fiber into the sheath.

9. The balloon catheter device of claim 3, further including a second valve near the proximal end of the sheath for connection to a balloon inflation source.

10. The balloon catheter device of claim 9, wherein a syringe is insertable in the second valve.

11. The balloon catheter device of claim 9, wherein water, saline or contrast agent is injected to inflate the balloon.

12. The balloon catheter device of claim 3, further comprising an inflation lumen through which the balloon inflation material travels to the balloon.

13. The balloon catheter device of claim 12, wherein the inflation lumen has a diameter ranging from about 100 to about 500 μm.

14. The balloon catheter device of claim 1, wherein the balloon of the balloon catheter device is made of an optically transparent, flexible, medical-grade silicone rubber.

15. The balloon catheter device of claim 1, wherein the balloon is made of a material optically transparent to laser radiation.

16. The balloon catheter device of claim 1, wherein the balloon of the balloon catheter device is capable of being inflated to 5- cc volume, 2- cm -diameter and 4-cm-length.

17. The balloon catheter device of claim 1, further comprising a high power energy source that provides approximately 10–100 W.

18. The balloon catheter device of claim 1, further comprising a high power energy source being configured and arranged so as to be capable of providing energy capable of producing thermal lesions in the pulmonary veins of a patient.

19. The balloon catheter device of claim 17 or 18, wherein the high power energy source is a laser.

20. The balloon catheter device of claim 19 wherein the laser is selected from a high-power diode laser array operating between about 600–1300 μm, Nd:YAG lasers operating at about 1.06 or 1.32 μm, and fiber lasers operating at about 1 μm.

21. The balloon catheter device of claim 1, wherein the balloon catheter device includes an optical fiber with a core size that ranges from about 400 to about 600 μm and a tip length ranging from about 5 to about 20 mm.

22. The balloon catheter device of claim 1, wherein the radial delivery mechanism comprises scattering particles embedded in the optical fiber.

23. The balloon catheter device of claim 22, wherein the scattering particles are selected from titanium dioxide and aluminum oxide scattering particles.

24. The balloon catheter device of claim 22, wherein the optical fiber is fabricated of a flexible silicone elastomer and the scattering particles are titanium dioxide scattering particles embedded in the distal tip of the optical fiber.

25. The balloon catheter device of claim 1, wherein the radial delivery mechanism comprises a frosted cap placed over the distal tip of the optical fiber.

26. The balloon catheter device of claim 1, wherein the radial delivery mechanism comprises a plurality of diffusing optical fibers.

27. The balloon catheter device of claim 26, wherein the plurality of diffusing optical fibers is arranged in a ring.

28. The balloon catheter device of claim 27, wherein the ring of diffusing optical fibers surrounds a guidewire.

29. The balloon catheter device of claim 1, wherein the radial delivery mechanism comprises an optically scattering solution.

30. The balloon catheter device of claim 29, wherein the optically scattering solution is injected into the balloon to inflate the balloon.

31. The balloon catheter device of claim 1, further comprising a reflective tip at the distal side of the balloon to assist in radial delivery of radiation.

32. The balloon catheter device of claim 1, wherein the radial delivery mechanism comprises at least one side-firing optical fiber that delivers radiation at about a 90 degree angle from the axis of the optical fiber.

33. The balloon catheter device of claim 1, wherein the radial delivery mechanism comprises a ring of fixed side-firing optical fibers.

34. The balloon catheter device of claim 1, further comprising an electrical measurement mechanism for determining if the pulmonary veins have been electrically isolated from the left atrium of a patient.

35. The balloon catheter device of claim 34, wherein the electrical measurement mechanism comprises electrodes on the surface of the balloon.

36. The balloon catheter device of claim 1, further comprising a temperature measurement mechanism for monitoring the temperature during the procedure.

37. The balloon catheter device of claim 36, wherein the temperature measurement mechanism comprises thermocouples embedded in the balloon wall.

38. A medical device kit, comprising one or more balloon catheter devices for treating arrhythmias attributable to atrial fibrillation, wherein each of the one or more balloon catheter devices includes:
  a shaft having a proximal end and a distal end;
  a balloon at the distal end of the shaft;
  wherein the balloon is configured and arranged so as to be in a deflated state when the balloon is being maneuvered and positioned proximal a pulmonary vein proximal the left atrium and is configured and arranged so the balloon is removably secured within the pulmonary vein proximal the left atrium when the balloon is in an inflated state;
  at least one optical fiber that extends through the shaft and balloon; and
  a radial delivery mechanism positioned inside of the balloon, wherein the radial delivery in mechanism and the at least one optical fiber area arranged so that visible or near-infrared radiation is radially delivered to a portion of the pulmonary vein, and at a power level sufficient to cause at least one of transmural, continuous and circumferential lesions to be formed in the pulmonary vein and thereby electrically isolating the pulmonary vein from the left atrium.

39. The kit of claim 38, wherein the one or more balloon catheter devices are packaged in sterile condition.

40. A method for treating a patient suffering from arrhythmias attributable to atrial fibrillation, comprising the steps:
  providing a balloon catheter device that includes:
  a shaft having a proximal end and a distal end,
  a balloon at the distal end of the shaft, wherein the balloon is configured and arranged so as to be removably secured within the pulmonary vein proximal the left atrium when the balloon is inflated for treatment,
  at least one optical fiber, extending through the shaft and balloon, and
  a radial delivery mechanism positioned inside of the balloon;
  positioning the balloon catheter device within the pulmonary vein proximal the left atrium for treatment;

inflating the balloon when the balloon catheter device so positioned so as to removably secure the balloon within the vein proximal the left atrium; and radially delivering visible or near-infrared radiation via the radial delivery mechanism to a portion of the pulmonary vein proximal the balloon at the treatment site so as to cause at least one of transmural, continuous and circumferential lesions to be formed in the portion of the pulmonary vein and so as to cause the pulmonary vein to be electrically isolated from the left atrium.

41. A method for treating a patient suffering from arrhythmias attributable to atrial fibrillation comprising the steps of:

providing a balloon catheter device including a shaft having a proximal end and a distal end; a balloon at the distal end of the shaft, wherein the balloon is configured and arranged so as to be removably secured within the pulmonary vein proximal the left atrium for treatment; at least one optical fiber, extending through the shaft and balloon, where the balloon is configured and arranged so when the balloon is in an inflated state the balloon is removably secured within the pulmonary vein proximal the left atrium; and a radial delivery mechanism positioned inside of the balloon:

creating transmural, continuous, and circumferential lesions in the pulmonary vein using the provided balloon catheter device.

42. The method of any one of claims 40 or 41, wherein the provided optical fiber comprises a visible or near-infrared radiation emitting optical fiber.

43. A method for treating a patient suffering from arrhythmias attributable to atrial fibrillation, comprising the steps of:

providing a balloon catheter device including a shaft having a proximal end and a distal end; a balloon at the distal end of the shaft, wherein the balloon catheter device is configured and arranged so as to be removably secured within a pulmonary vein proximal the left atrium; at least one optical fiber, extending through the shaft and balloon; and a radial delivery mechanism positioned inside of the balloon;

making an incision to provide access to the pulmonary vein;

inserting the balloon catheter device into the incision and into a blood vessel;

directing the balloon catheter device through the blood vessel to the pulmonary vein and so as to be proximal the left atrium;

inflating the balloon; and delivering visible or near-infrared radiation radially from the optical fiber to a portion of the pulmonary vein via the radial delivery mechanism, so as to electrically isolate the pulmonary vein from the left atrium.

44. The method of claim 40, wherein the step of delivering visible or near-infrared radiation radially to the pulmonary vein includes forming transmural, continuous, and circumferential lesions in the pulmonary veing.

45. The method of any one of claims 40 or 44, further comprising the step of making an electrical measurement to determine whether electrical isolation of the pulmonary vein from the left atrium has been accomplished.

46. The method of any one of claims 40 or 44, further comprising the step of maintaining the temperature in a range of from about 50° C. to about 80° C.

47. The balloon catheter device of claim 1, wherein the balloon catheter device includes an optical fiber made of a silica core and cladding protected with a teflon-coated jacket.

* * * * *